United States Patent [19]

Bradford et al.

[11] Patent Number: Plant 7,064

[45] Date of Patent: Dec. 5, 1989

[54] NECTARINE TREE (FIRE DIAMOND)

[76] Inventors: Norman G. Bradford, 11875 E. Savana Rd.; Lowell G. Bradford, 12439 E. Savana Rd., both of Le Grand, Calif. 95333

[21] Appl. No.: 294,104

[22] Filed: Jan. 6, 1989

[51] Int. Cl.[4] ..... A01H 5/00

[52] U.S. Cl. ..... Plt./41

[58] Field of Search ..... Plt./41

[56] References Cited

U.S. PATENT DOCUMENTS

P.P. 5,438 4/1985 Bradford ..... Plt. 41

*Primary Examiner*—James R. Feyrer

[57] ABSTRACT

The present invention relates to a nectarine tree and more particularly to a new and distinct variety broadly characterized by a medium size, medium vigor, hardy, very productive and regular bearing tree. The fruit matures under the ecological conditions described approximately the second week in May, with first picking on May 10, 1988, making it a very early ripening variety. The fruit is uniform but small in size, semi-freestone in type, dark red in skin color, and a mild balance of acid and sugar in flavor. The variety was developed as a hybridized seedling from the selected seed parent, Early Diamond (U.S. Plant Pat. No. 5,438), and an unnamed genetically dwarf peach seedling as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Fire Diamond". The present variety was hydridized in 1983 by us in a cultivated area of our experimental orchard at Bradford Farms near Le Grand, Calif. in Merced County (San Joaquin Valley). It was the result of a seedling using Early Diamond (U.S. Plant Pat. No. 5,438) as the selected seed parent and an unnamed dwarf peach seedling as the selected pollen parent. Subsequent to origination of the present variety of nectarine tree, we asexually reproduced it by budding and grafting, and such reproduction of plant and fruit characteristics were true to the original plant in all respects.

The fruit produced by the present variety most nearly resembles the fruit of the seed parent, Early Diamond (U.S. Plant Pat. No. 5,438), by being early in ripening, good in flavor, globose in shape, and almost full red in color at harvest time, but is most distinguished therefrom and an improvement thereon by harvesting 21 days earlier, making it one of the earliest ripening nectarines presently known. It is further distinguished from the Early Diamond by having purplish red blossoms instead of pink blossoms and by having mostly reddish brown leaves instead of green leaves from mid-summer to dormancy.

DRAWING

The accompanying color photograph shows typical leaves, whole fruits exhibiting characteristic skin color and form, and a fruit divided near its suture plane showing the flesh and kernel, all of the subject variety.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of eating ripe on May 15, 1988, unless otherwise denoted. All major color code designations are by reference to the Inter-Society Color Council, National Bureau of Standards. Common color names are also used occasionally.

TREE

Size: Medium.
Vigor: Medium.
Growth: Spreading and dense.
Form: Vase formed.
Hardiness: Hardy.
Production: Very productive.
Bearing: Regular bearer.
Trunk:
- *Size.*—Medium.
- *Texture.*—Medium.
- *Color.*—Borwnish gray [64. brGy].
- *Lenticels.*—Numerous. Color: Moderate brown [58. m.Br]. Average Size: ¼" [6.096 mm.].

Branches:
- *Size.*—Medium.
- *Texture.*—Medium.
- *Color.*—1st Year Wood — Topside: Moderate pink [5. m.Pk] in sunlight. 1st Year Wood — Underside: Light yellow green [119. l.YG]. Older Wood: Strong brown [55. s.Br].
- *Lenticels.*—Numerous, very small.

Leaves:
- *Size.*—Medium. Average Length: 5" [127 mm.]. Average Width: 1¼" [31.75 mm.].
- *Thickness.*—Medium.
- *Form.*—Elliptical.
- *Apex.*—Acutely pointed.
- *Base.*—Acute.
- *Surface.*—Smooth.
- *May color.*—Dorsal surface: Moderate olive green [125. m.OlG] with dark purplish red [259. d.pR] blended along the edges and tips, especially on new growth. Ventral surface: Moderate yellow green [120. m.YG], with dark purplish red [259. d.pR] blended along the edges and tips.

*August color.*—Dorsal surface: Grayish reddish brown [46. gy.rBr] edging smoothly blending into a strong yellow green [117. s.YG] center. Ventral surface: Grayish reddish brown [46. gy.rBr].

*Margin.*—Finely serrate.

*Venation.*—Pinnately net veined.

*Petiole.*—Average Length: ⅜" [9.53 mm.]. Average Thickness: 1/16" [1.588 mm.].

*Glands.*—Numbers: 2 to 4 per leaf. Position: Most are oppositely positioned on petiole and base of blade. Size: Small. Form: Globose. May Color: Deep greenish yellow [100. deep gY]. August Color: Dark purplish red [259. d.pR].

*Stipules.*—Numerous. Average Length: ¼" [6.35 mm.].

Flower buds:

*Hardiness.*—Hardy.

*Size.*—Medium.

*Length.*—Medium.

*Form.*—Free.

*Surface.*—Pubescent.

Flowers:

*Blooming period.*—Medium, as compared with other varieties.

*Size.*—Large, with some double blossoms.

*Color.*—Moderate purplish red [258. m.pR].

FRUIT

Maturity when described: Eating ripe, May 15, 1988.

Date of first picking: May 10, 1988.

Date of last picking: May 16, 1988.

Size: Uniform, small.

*Average diameter axially.*—2¼" [57.15 mm].

*Average traversely in suture plane.*—2⅛" [53.98 mm].

Form: Uniform, symmetrical, globose.

*Longitudinal section form.*—Circular.

*Transverse section through diameter.*—Elliptical, with slight compressing at suture.

Suture: An inconspicuous line extending from the base and discontinuing at the apex.

Ventral surface: Rounded slightly.

Lips: Very slightly lipped.

Cavity: Flaring and circular with suture plane showing on one side.

Base: Rounded and slightly cuneate.

Apex: Rounded.

Pistil point: Apical, short in length.

Stem: Small.

*Average length.*—¼" [6.35 mm.].

*Average width.*—⅛" [3.175 mm.].

Skin:

*Thickness.*—Medium.

*Texture.*—Medium.

*Tenacity.*—Tenacious to flesh.

*Tendency to crack.*—Very strong in wet years.

*Color.*—Pigmentation first appears as very deep red [14. v.deep R] dots over a brilliant yellow [83. brill.Y] background, with most fruits reaching this full red color and having some brilliant orange yellow [67. brill.OY] freckling at picking ripeness.

Flesh:

*Color.*—Brilliant yellow [83. brill.Y] to the pit.

*Surface of the pit cavity.*—Free of streaking.

*Amygdalin.*—Moderate.

*Juice.*—Abundant, watery.

*Texture.*—Medium firm, fine, crisp.

*Fibers.*—Few, fine, tender.

*Ripens.*—Mostly even, but slightly earlier at apex.

*Flavor.*—A mild balance of acid and sugar.

*Aroma.*—Pronounced.

*Eating quality.*—Very good.

STONE

Type: Semi-freestone.

Form: Oblong.

Base: Oblique.

Apex: Acute.

Sides: Equal.

Surface: Irregularly furrowed throughout, ridged toward the apex, and pitted toward the base.

Ridges: Jagged.

Color: Pale orange yellow [73. p.OY].

Pit wall: 3/16" [4.763 mm.] thick.

Tendency to split: Strong, but most are internally concealed.

Kernel:

*Form.*—Oval.

*Taste.*—Bitter.

*Viable.*—Yes, using embryoculture techniques.

*Average width.*—7/16" [11.11 mm.].

*Average length.*—11/16" [17.46 mm.].

Pellicle color: Dark pink [6. d.Pk].

Amygdalin: Moderate.

USE

Market: Fresh and long distance shipping.

Keeping quality: Good.

Shipping quality: Good.

Resistance to insects: No unusual susceptibilities noted.

Resistance to diseases: Susceptibilities to blossom brownrot during wet blooming seasons.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct very early ripening variety of semi-freestone nectarine tree, substantially as illustrated and described, which most nearly resembles the Early Diamond (U.S. Plant Pat. No. 5,438) nectarine variety by producing fruit that is good in flavor, globose in shape, and almost full red in color at harvest time, but is distinguished therefrom and an improvement thereon by harvesting 21 days earlier, making it one of the earliest ripening nectarines presently known, and is further distinguished from the Early Diamond by having purplish red blossoms instead of pink blossoms and by having mostly reddish brown leaves instead of green leaves from mid-summer to dormancy.

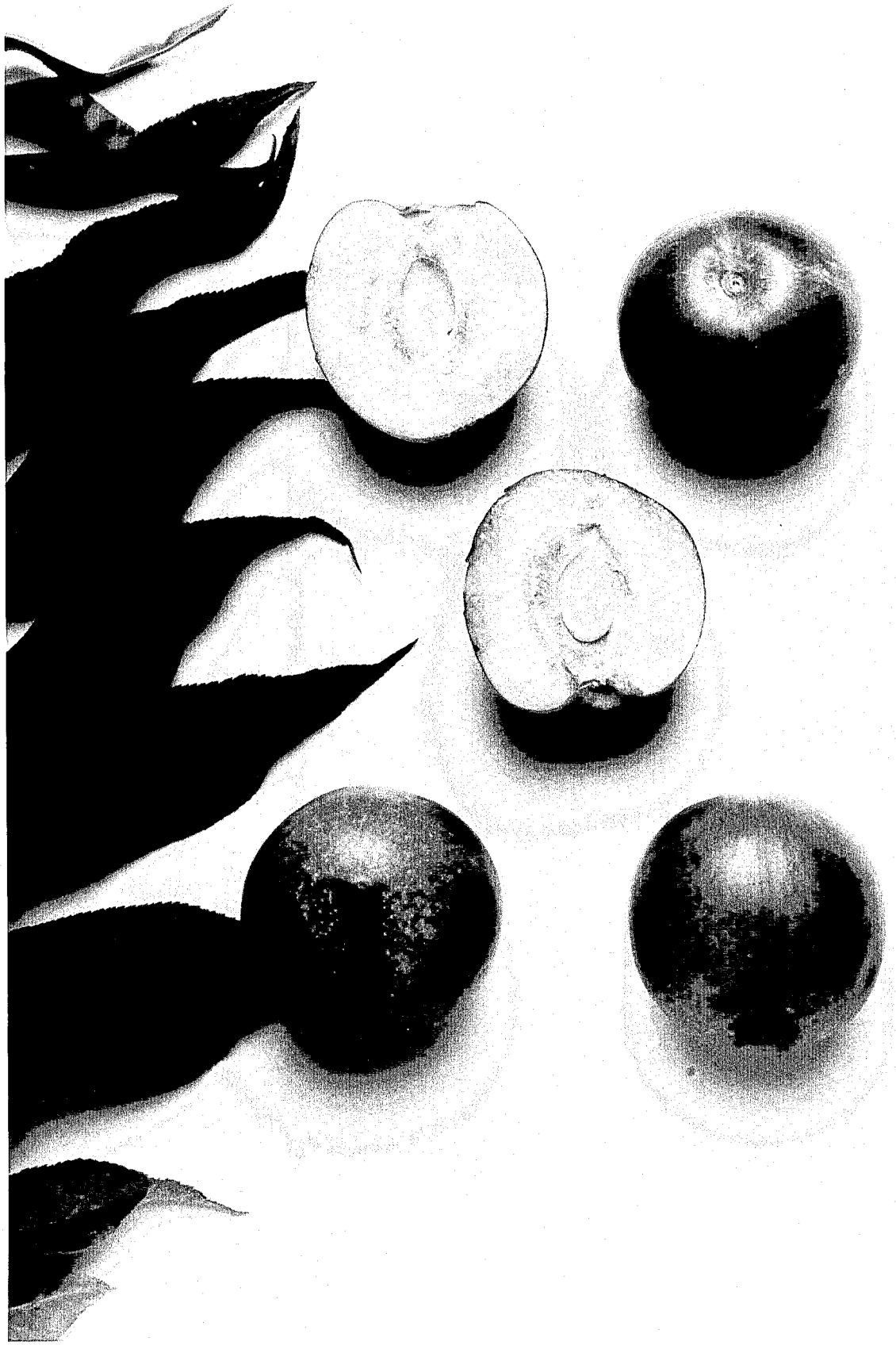

* * * * *